United States Patent [19]

Koster

[11] Patent Number: 4,587,051
[45] Date of Patent: May 6, 1986

[54] DESULFONATION PROCESS FOR PREPARING 2-AZETIDINONES

[75] Inventor: William H. Koster, East Amwell, N.J.

[73] Assignee: E. R. Squibb & Sons, Inc., Princeton, N.J.

[21] Appl. No.: 612,192

[22] Filed: May 21, 1984

Related U.S. Application Data

[63] Continuation-in-part of Ser. No. 514,730, Jul. 18, 1983, abandoned.

[51] Int. Cl.[4] .................. C07D 205/08; C07D 403/04; C07D 401/04; C07D 405/04
[52] U.S. Cl. .............................. 260/239 A; 544/335; 544/359; 546/192; 544/364; 544/366; 546/194; 544/317; 544/367; 546/207; 544/369; 544/370; 546/209; 544/371; 546/210; 544/372; 544/374; 546/211; 544/379; 544/182; 546/212; 544/215; 544/279; 546/213; 544/295; 546/276; 546/278; 544/296; 546/279; 546/280; 544/300; 544/301; 546/281; 544/310; 544/311; 546/283; 544/312; 544/316; 546/284; 260/239.3 R; 546/187; 260/243.3; 260/244.4; 546/208; 260/245.4; 260/245.5; 546/256; 260/245.6; 260/245.7; 546/275; 260/330.3; 544/319; 544/320; 544/321; 544/322; 544/323; 544/324; 544/325; 544/326; 544/327; 544/331; 544/332; 544/333; 544/334
[58] Field of Search ......... 260/245.4, 239 A, 239.3 R, 260/243.3, 244.4, 245.5, 245.6, 245.7, 330.3, 330.9; 514/182, 215, 279, 295, 296, 300, 301, 302, 310, 311, 316, 317, 319, 320, 321, 322, 323, 324, 325, 326, 327, 331, 332, 333, 334, 335, 359, 364, 366, 367, 369, 370, 371, 372, 374, 379; 546/187, 194, 207, 208, 209, 210, 211, 212, 213, 256, 275, 276, 278, 279, 280, 281, 283, 284

[56] References Cited

FOREIGN PATENT DOCUMENTS 0062876 10/1982 European Pat. Off. .
0061765 10/1982 European Pat. Off. .
2071650 9/1981 United Kingdom .
2104069 3/1983 United Kingdom .

OTHER PUBLICATIONS

Hünig et al., Liebigs. Ann. Chem. 708, 170–177 (1967).

Primary Examiner—Mark L. Berch
Attorney, Agent, or Firm—Lawrence S. Levinson; Donald J. Barrack

[57] ABSTRACT

A compound having the formula

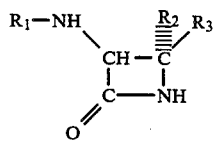

can be prepared by heating an anion having the formula

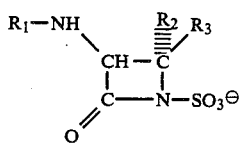

with a cation having the formula

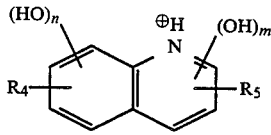

or a cation having the formula

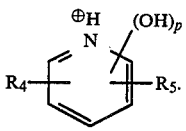

20 Claims, No Drawings

DESULFONATION PROCESS FOR PREPARING 2-AZETIDINONES

This application is a continuation-in-part of co-pending U.S. patent application Ser. No. 514,730, filed July 18, 1983, and now abandoned.

BACKGROUND OF THE INVENTION

Recently, there has been a concentrated research effort in the field of monocyclic β-lactam antibiotics. Discoveries of antibacterial agents have included 3-acylamino-2-azetidinones having in the 1-position a (i) sulfonic acid salt substituent (see, for example, United Kingdom Pat. No. 2,071,650, published Sept. 23, 1981); (ii) [(substituted sulfonyl)amino]carbonyl substituent (see European patent application No. 62,876, published Oct. 20, 1982); (iii) phosphinic or phosphonic acid substituent (see European patent application No. 61,765, published Oct. 6, 1982); and (iv) (acylamino)sulfonyl substituent (see United Kingdom Pat. No. 2,104,069, published Mar. 2, 1983). These β-lactams can be represented by the structural formula

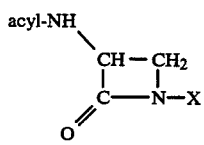

(optionally substituted in the 4-position) wherein X is one of the activating groups described above.

Various processes are described in the cited references for preparing β-lactams of the above structural formula. One such method involves the addition of the activating group ("X") to the corresponding β-lactam having the formula

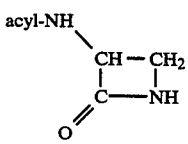

(optionally substituted in the 4-position).

BRIEF DESCRIPTION OF THE INVENTION

A compound having the formula

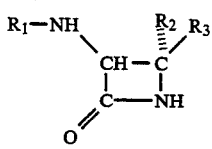   I can be prepared by heating together an anion having the formula

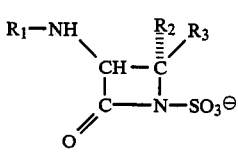   II and a cation having the formula

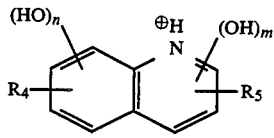   III or

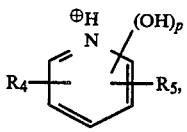   IV provided, however, that if in formula III n and m are each 0 or in formula IV p is 0, a nucleophile having the formula $R_6$—OH   V must also be present.

As used in the above formulas, and throughout the specification, the symbols are as defined below:

$R_1$ is an acyl group derived from a carboxylic acid;

$R_2$ and $R_3$ are the same or different and each is hydrogen, alkyl, alkenyl, alkynyl, cycloalkyl, phenyl, substituted phenyl or a 4, 5, 6 or 7-membered heterocycle (referred to hereinafter as $R_x$) or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —$CH_2X_1$ [wherein $X_1$ is azido, amino (—$NH_2$), hydroxy, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

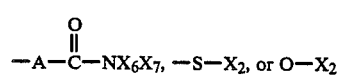

(wherein A, $X_2$, $X_6$ and $X_7$ are as hereinafter defined)], —S—$X_2$ or O—$X_2$ [wherein $X_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

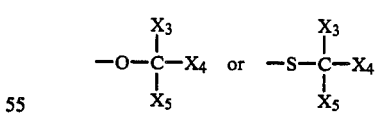

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

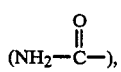

(substituted amino)carbonyl, or cyano

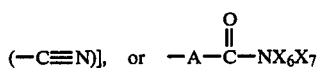

(wherein A is —CH=CH—, —(CH$_2$)$_n$—, —CH$_2$—O—, —CH$_2$—NH—, or —CH$_2$—S—CH$_2$—, n is 0, 1 or 2, and X$_6$ and X$_7$ are the same or different and each is hydrogen, alkyl, phenyl or substituted phenyl, or X$_6$ is hydrogen and X$_7$ is amino, substituted amino, alkanoylamino or alkoxy, or X$_6$ and X$_7$ when taken together with the nitrogen atom to which they are attached form a 4, 5, 6 or 7-membered heterocycle);

R$_4$ and R$_5$ are the same or different and each is hydrogen, alkyl, substituted alkyl, phenyl, substituted phenyl, halogen, alkoxy, phenyloxy, (phenylcarbonyl)oxy, alkanoyloxy, alkanoylamino, or (phenylcarbonyl)amino;

R$_6$ is hydrogen, alkyl, or phenyl;

n is 0 or 1, m is 0 or 1 and the sum of n+m is 0 or 1; and p is 0 or 1.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3, 4, 5, 6 or 7 carbon atoms.

The term "substituted alkyl" refers to alkyl groups substituted with one, or more, azido, amino (—NH$_2$), halogen, hydroxy, carboxyl, cyano, alkoxycarbonyl, aminocarbonyl, alkanoyloxy, alkoxy, phenyloxy, (substituted phenyl)oxy, R$_x$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), or carboxyl groups.

The term "substituted amino" refers to a group having the formula —NY$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy, or amino (—NH$_2$).

The expression "a 4,5,6 or 7-membered heterocycle" (referred to as "R$_x$") refers to substituted and unsubstituted, aromatic and non-aromatic groups containing one or more nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3,-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, Cephalosporins and Penicillins, edited by Flynn, Academic Press (1972), German Offenlegungsschrift No. 2,716,677 published Oct. 10, 1978, Belgian Pat. No. 867,994, published Dec. 11, 1978, U.S. Pat. Nos. 4,152,432, issued May 1, 1979, 3,971,778, issued July 27, 1976, 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

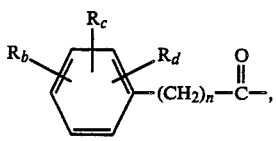

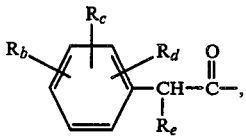

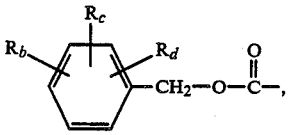

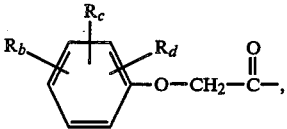

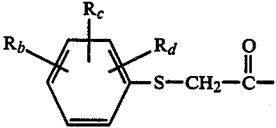

or

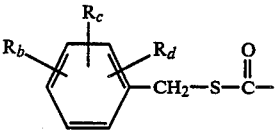

wherein n is 0, 1, 2 or 3; $R_b$, $R_c$, and $R_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

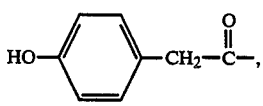

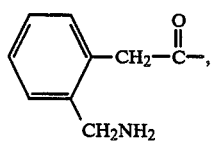

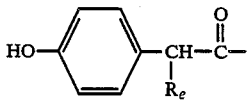

($R_e$ is preferably a carboxyl salt or sulfo salt) and

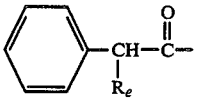

($R_e$ is preferably a carboxyl salt or sulfo salt).

(c) Heteroaromatic groups having the formula

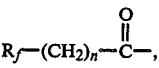

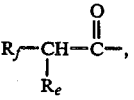

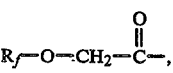

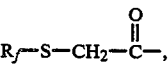

$$R_f-\overset{O}{\underset{\|}{C}}-\overset{O}{\underset{\|}{C}}-,$$

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

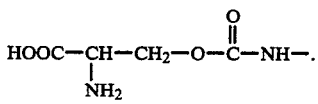

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

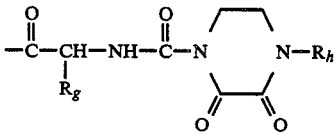

wherein $R_g$ is an aromatic group (including carbocyclic aromatics such as those of the formula

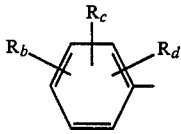

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino (i.e., $$-NH-\overset{O}{\underset{\|}{C}}-R_g$$

wherein $R_g$ is as defined above) or alkylcarbonylamino.

Preferred [[(4-substituted-2,3-dioxo-1-piperazinyl)-carbonyl]amino]arylacetyl groups include those wherein $R_h$ is ethyl, phenylmethyleneamino or 2-furylmethyleneamino.

(e) (Substituted oxyimino)arylacetyl groups having the formula $$-\overset{O}{\underset{\|}{C}}-\underset{\underset{R_g}{|}}{C}=N-O-R_i$$

wherein $R_g$ is as defined above and $R_i$ is hydrogen, alkyl, cycloalkyl, alkylaminocarbonyl, arylaminocarbonyl (i.e., $$-\overset{O}{\underset{\|}{C}}-NH-R_g$$

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, dialkoxyphosphinyl or tetrazolyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula $$-\overset{O}{\underset{\|}{C}}-\underset{\underset{R_g}{|}}{CH}-NH-\overset{O}{\underset{\|}{C}}-R_j$$

wherein $R_g$ is as defined above and $R_j$ is

<p style="text-align:center">[structure with $R_b$, $R_c$, $R_d$ on ring and —(CH$_2$)$_n$—O—]</p> amino, alkylamino, (cyanoalkyl)amino, amido, alkylamido, (cyanoalkyl)amido,

[structures shown:]

—CH$_2$—NH—C(=NH)— [pyridyl],   N—CH(NH$_2$)—CH$_2$—C(=O)—NH—CH$_3$,

[phenyl-N=/OH ring]—[phenyl]—SO$_2$—N(CH$_2$—CH$_2$—OH)$_2$,

[HO-pyridyl-CH$_3$],   [OH-naphthyridine],

[OH-pyridyl-CH=N-piperazinyl-N—CH=O], or

[HO, HO-chromone-C(=O)—]

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula $$-\overset{O}{\underset{\|}{C}}-\underset{\underset{R_g}{|}}{CH}-NH-\overset{O}{\underset{\|}{C}}-N\underset{\underset{CH_2-CH_2}{|\quad\quad|}}{\overset{\overset{O}{\|}}{\underset{}{C}}}N-R_k$$

wherein $R_g$ is as defined above and $R_k$ is hydrogen, alkylsulfonyl, arylmethyleneamino (i.e., —N=CH—$R_g$ wherein $R_g$ is as defined above), $$-\overset{O}{\underset{\|}{C}}-R_m$$

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts", when used to describe a β-lactam, refer to basic salts formed with inorganic and organic bases. Such salts include ammonium salts, alkali metal salts like sodium and potassium salts, alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, because this invention deals with the preparation of chemical intermediates, not final products to be used as medicines.

Salts of an azetidinone-1-sulfonic acid are formed by reacting the free acid form of the sulfonate with one or more equivalents of an appropriate base providing the desired cation in water or in a solvent mixture containing water. The salt is isolated by removal of solvent in vacuo or, in the case of water, by lyophilization. The free acid of the sulfonate is formed by treating an azetidinone-1-sulfonic acid salt with an insoluble sulfonic acid such as a cation exchange resin in the hydrogen form (e.g. a polystyrene sulfonic acid resin like Dowex 50).

Alternatively, salts may be formed by cation interchange. A salt of a β-lactam compound soluble in an organic solvent is combined with a salt containing the desired cation, also soluble in the same solvent system. The solvent system is chosen so that the formed salt is much less soluble than either of the added salts and thus precipitates from the medium and is collected.

The terms "salt" and "salts", when used to describe a quinoline compound or pyridine compound refer to acid-addition salts formed with inorganic and organic acids. Illustrative salts are the hydrohalides (especially the hydrochloride and hydrobromide), sulfate, nitrate, phosphate, tartrate, maleate, citrate, salicylate, methane-sulfonate, benzenesulfonate, toluenesulfonate and the like.

DETAILED DESCRIPTION OF THE INVENTION

It has been found that a cation of formula III or IV, which contains a hydroxy substituent, will associate with the sulfonate anion of formula II and then serve as a nucelophile and protic source for removal of the sulfonate group. Alternatively, an external nucleophile (i.e., a compound of formula V) can be used in conjunction with a cation of formula III or IV which does not contain a hydroxy substituent. This new methodology for the preparation of compounds of formula I affords a general synthesis for the preparation of monocyclic β-lactam antibiotics such as those mentioned above under the heading "Background of the Invention".

In one embodiment of this invention, both the anion of formula II and cation of formula III or IV are in the form of a salt having the formula

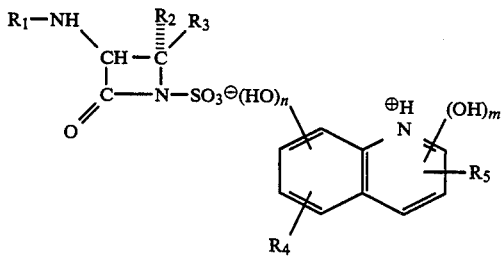

or

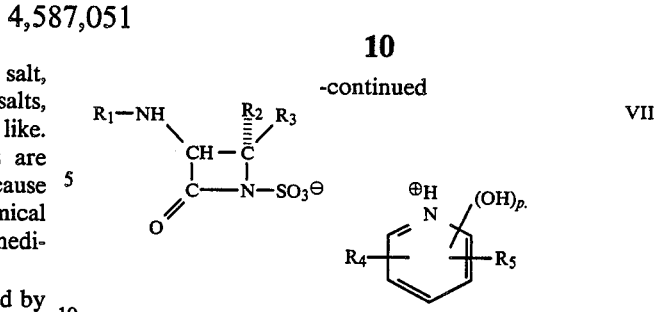

A salt of formula VI or VII can be heated in an organic solvent (e.g., ethanol, acetone, acetonitrile or others in which it has some solubility) to yield the desired 2-azetidinone of formula I. In the case of a salts wherein the cationic portion does not contain a hydroxy group, the heating must be done in the presence of a nucleophile of formula V.

In another embodiment of this invention, the anion of formula II is in the form of a salt of a compound having the formula

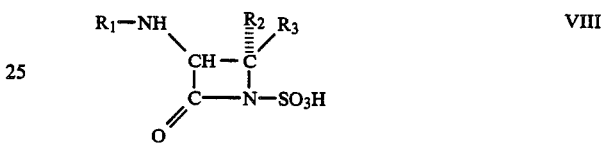

and the cation of formula III or IV is in the form of a salt of a compound having the formula

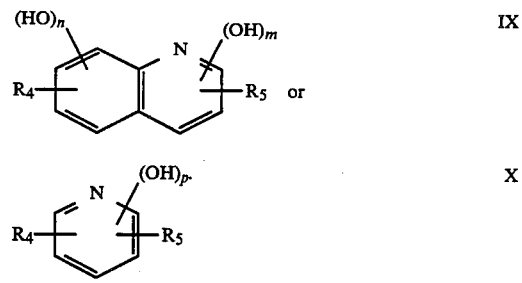

The salt of a compound of formula VIII can be dissolved in an organic solvent, combined with a salt of formula IX or X and heated to yield the desired 2-azetidinone of formula I. In those reactions wherein the salts of formulas IX and X do not contain a hydroxy group, the heating must be done in the presence of a nucleophile of formula V.

A salt of formula VI or VII can be prepared using known methodology from β-lactam compounds of formula VIII and salts thereof. The β-lactam compounds of formula VIII exist in their most stable form as salts (including inner salts). In dilute aqueous solution, they also exist as acids. The acid form, in an aqueous solution, can be obtained by passage of a corresponding salt through an ion-exchange resin (acid form).

If the acid form of a compound of formula VIII is used as a precursor to a compound of formula VI or VII, a compound of formula IX or X is first added to a solution of the acid in water containing a miscible organic solvent (e.g., acetone or acetonitrile), which upon removal of the solvent mixture yields the corresponding salt.

A salt of formula VI or VII can also be prepared from salts of compounds of formula VIII using the cation interchange methodology described above under the description of the terms "salt" and "salts".

The following examples are specific embodiments of this invention.

EXAMPLE 1

(3S-trans)-3-[[(Phenylmethoxy)carbonyl]amino]-4-methyl-2-azetidinone

Method I (A)

(3S-trans)-2-Oxo-3-[[(phenylmethoxy)carbonyl]amino]-4-methyl-1-azetidinesulfonic acid, 8-hydroxyquinolinium salt (3S-trans)-2-Oxo-3-[[(phenylmethoxy)carbonyl]amino]-4-methyl-1-azetidinesulfonic acid, tetrabutylammonium salt (500 mg, 0.9 mmol) was dissolved in a mixture of water and acetonitrile. The solution was passed through an AGMP-50 ion-exchange resin column (H$\oplus$ form, 7 ml, 1.7 meq/ml) eluting with water. The eluate was run into a flask containing 8-hydroxyquinoline (131 mg, 0.9 mmol). Acetonitrile was removed from the resulting solution under reduced pressure at <35° C. and the remaining aqueous solution was lyophilized yielding a solid. Trituration with ether and drying in vacuo afforded the desired product as a yellow powder (398 mg), melting point 61°–68° C.

Analysis Calc'd. for $C_{21}H_{21}N_3O_7S.0.7H_2O$ (472.17): C, 53.42; H, 4.78; N, 8.90; S, 6.79; Found: C, 53.42; H, 4.48; N, 8.98; S, 6.68.

(B)

(3S-trans)-3-[[(Phenylmethoxy)carbonyl]amino]-4-methyl-2-azetidinone

A solution of (3S-trans)-2-oxo-3-[[(phenylmethoxy)carbonyl]amino]-4-methyl-1-azetidinesulfonic acid, 8-hydroxyquinolinium salt (150 mg, 0.326 mmol) in acetonitrile (10 ml) was brought rapidly to reflux by lowering the reaction vessel into a preheated oil bath. The mixture was refluxed for a total of 9 minutes during which time a precipitate formed. After cooling to room temperature, the mixture was filtered and solvent was removed from the filtrate in vacuo. The resulting residue was partially dissolved in a small amount of acetonitrile and the addition of ethyl acetate caused further precipitation. After decanting the supernatant, the procedure was repeated on the solid. The remaining solid was triturated with ethyl acetate and decanted. The supernatants were filtered through Celite, combined, and solvent was removed under reduced pressure yielding an oil (84 mg). The crude product was purified by column chromatography on silica gel (2 g, Mallinckrodt SilicAR CC-4). Elution with 5% acetonitrile: 95% ethyl acetate afforded the desired product (56 mg).

Method II

Following the procedure of Method I, part A, but utilizing 4-hydroxyquinoline in place of 8-hydroxyquinoline, yielded (3S-trans)-3-[[(phenylmethoxy)carbonyl]amino]-4-methyl-1-azetidinesulfonic acid, 4-hydroxyquinolinium salt as a colorless solid (after lyophilization), melting point 58°–66° C.

Analysis Calc'd. for $C_{21}H_{21}N_3O_7S$ (MW 459.47): C, 54.89; H, 4.69; N, 9.14; S, 6.98; Found: C, 54.81; H, 4.81; N, 9.24; S, 6.34.

This salt (46 mg) was heated at reflux in acetonitrile (2 ml) for 4 hours. Formation of the title compound was verified by thin layer chromatography (Merck silica gel 60F, 3:1:1 butanol:acetic acid:water).

Method III

Following the procedure of Method I, part A, but utilizing 5-hydroxyquinoline in place of 8-hydroxyquinoline, yielded (3S-trans)-3-[[(phenylmethoxy)carbonyl]amino]-4-methyl-1-azetidinesulfonic acid, 5-hydroxyquinolium salt, melting point 55°–64° C.

Analysis Calc'd. for $C_{21}H_{21}N_3O_7S.0.55H_2O$ (469.44): C, 53.73; H, 4.75; N, 8.95; Found: C, 53.73; H, 4.59; N, 9.18.

This salt (115 mg) was dissolved in dry acetonitrile (5 ml) and the resulting solution was heated at reflux for 0.5 hours. After cooling, solvent was removed in vacuo and the residue was dissolved in an ethyl acetate (6 ml)-water (3 ml) mixture. After addition of magnesium sulfate (68 mg) and sodium bicarbonate (63 mg), the mixture was shaken. The organic layer was separated, washed with water (3 ml), and dried (magnesium sulfate). Solvent was removed in vacuo, the residue was dissolved in acetonitrile, and the insolubles were removed by filtration. Solvent was removed under reduced pressure and the residue was chromatographed on silica gel (Mallinckrodt SilicAr CC-7). Elution with ethyl acetate yielded (3S-trans)-2-oxo-3-[[(phenylmethoxy)carbonyl]amino]-4-methyl-2-azetidinone (27 mg).

Method IV (A)

(3S-trans)-2-Oxo-3-[[(phenylmethoxy)carbonyl]amino]-4-methyl-1-azetidinesulfonic acid, pyridinium salt Following the procedure of Method I, part A, but utilizing pyridine in place of 8-hydroxyquinoline, yielded (3S-trans)-3-[[(phenylmethoxy)carbonyl]amino]-4-methyl-1-azetidinesulfonic acid, pyridinium salt as a colorless solid (after lyophilization), melting point 56°–64° C.

Analysis Calc'd. for $C_{16}H_{17}N_3O_6$ (MW 379.99): C, 50.65; H, 4.52; N, 11.08; S, 8.45; Found: C, 50.33; H, 4.55; N, 10.80; S, 8.09.

(B)

(3S-trans)-3-[[(Phenylmethoxy)carbonyl]amino]-4-methyl-2-azetidinone (3S-trans)-2-Oxo-3-[[(phenylmethoxy)carbonyl]amino]-4-methyl-1-azetidinesulfonic acid, pyridinium salt (190 mg, 0.5 mmol) was dissolved in dry acetonitrile (10 ml), phenol (47 mg, 0.5 mmol) was added, and the mixture was refluxed for 4 hours. Solvent was removed in vacuo, the residue was dissolved in an ethyl acetate-water mixture and shaken after addition of magnesium sulfate (136 mg) and sodium bicarbonate (126 mg). The ethyl acetate layer was separated, washed with water, and dried (magnesium sulfate). Solvent was removed in vacuo, and the residue was purified by column chromatography on silica gel (Mallinckrodt SilicAr CC-7). Elution with ethyl acetate yielded (3S-trans)-2-oxo-3-[[(phenylmethoxy)carbonyl]amino]-4-methyl-2-azetidinone (24 mg).

Method V (3S-trans)-2-Oxo-3-[[(phenylmethoxy)carbonyl]-amino]-4-methyl-1-azetidinesulfonic acid, pyridinium salt (393 mg, 0.1 mmol; see Method IVA) was dissolved in absolute ethanol (20 ml) and refluxed for 4 hours. The reaction mixture was cooled to room temperature and ethanol was removed in vacuo. The residue was purified by column chromatography on silica gel (Mallinckrodt SilicAr CC-7). Elution with ethyl acetate yielded (3S-trans)-2-oxo-3-[[(phenylmethoxy)carbonyl]-amino]-4-methyl-2-azetidinone as an oil (152 mg).

Method VI (3S-trans)-2-Oxo-3-[[(phenylmethoxy)carbonyl]amino]-4-methyl-1-azetidinesulfonic acid, 8-hydroxyquinolinium salt (230 mg, 0.5 mmol; see Method IA) was dissolved in absolute ethanol (10 ml) and refluxed for 4 hours. Ethanol was removed in vacuo yielding a residue which was triturated with ethyl acetate (5×10 ml). From the combined extract, solvent was removed in vacuo affording a residue which was chromatographed on silica gel (Mallinckrodt CC-7). Elution with ethyl acetate yielded (3S-trans)-3-[[(phenylmethoxy)-carbonyl]amino]-4-methyl-2-azetidinone (98 mg).

Method VII (3S-trans)-2-Oxo-3-[[(phenylmethoxy)carbonyl]amino]-4-methyl-1-azetidinesulfonic acid, 5-hydroxyquinolinium salt (230 mg, 0.5 mmol; see Method III) was treated as described in Method VI to yield the desired (3S-trans)-3-[[(phenylmethoxy)carbonyl]amino]-4-methyl-2-azetidinone (87 mg).

EXAMPLE 2

(3S)-3-[[(Phenylmethoxy)carbonyl]amino]-2-azetidinone

Method I (A)

(3S)-2-Oxo-3-[[(phenylmethoxy)carbonyl]amino]-1-azetidinesulfonic acid, 8-hydroxyquinolinium salt From (3S)-2-oxo-3-[[(phenylmethoxy)carbonyl]amino]-1-azetidinesulfonic acid, tetrabutylammonium salt (600 mg, 1.13 mmol) the desired product was obtained as a yellow powder (467 mg) following the procedure described in Example 1A, method I, part A.

(B)

(3S)-3-[[(Phenylmethoxy)carbonyl]amino]-2-azetidinone (3S)-2-Oxo-3-[[(phenylmethoxy)carbonyl]amino]-1-azetidinesulfonic acid, 8-hydroxyquinolinium salt (150 mg, 0.337 mmol) was added to acetonitrile (10 ml) and rapidly heated to reflux in a preheated oil bath. After refluxing for a total of 18 minutes, the mixture was cooled to room temperature, filtered through Celite, and solvent was removed in vacuo. The residue was extracted with an acetonitrile-ethyl acetate mixture and the extract chromatographed on a silica gel column (Mallinckrodt SilicAR CC-7). The desired product (31 mg) was eluted with a 5% acetonitrile:95% ethyl acetate mixture.

Method II (A) 8-Hydroxyquinolinium, p-toluenesulfonate

The toluenesulfonic acid salt of 8-hydroxyquinoline was formed by dissolving toluenesulfonic acid monohydrate (1.9 g, 10 mmol) in acetonitrile and adding 8-hydroxyquinoline (1.45 g, 10 mmol). Removal of solvent in vacuo and addition of ether to the residual oil results in crystallization. Trituration several times with ether followed by drying in vacuo yields 8-hydroxyquinolinium, p-toluenesulfonate as a powder (3.11 g).

(B)

(3S)-3-[[(Phenylmethoxy)carbonyl]amino]-2-azetidinone

To a solution of (3S)-2-oxo-3-[[(phenylmethoxy)carbonyl]amino]-1-azetidinesulfonic acid, tetrabutylammonium salt in acetonitrile was added 8-hydroxyquinolinium p-toluenesulfonate. The mixture was refluxed, yielding the title compound as verified by thin layer chromatography (Merck silica gel 60F, ethyl acetate).

Method III (A)

(3S)-2-Oxo-3-[[(Phenylmethoxy)carbonyl]amino]-1-azetidinesulfonic acid, 8-hydroxyquinolinium salt To a stirred solution of 3.58 g of (3S)-2-oxo-3-[[(phenylmethoxy)carbonyl]amino]-1-azetidinesulfonic acid, tetrabutylammonium salt and 960 mg of 8-hydroxyquinoline in 10 ml of dichloroethane was added 1.53 g of camphorsulfonic acid. An additional 5 ml of dichloroethane was added and the mixture was stirred to effect solution and a seed crystal of the desired product was added to initiate precipitation. After ca. 5 minutes, 15 ml of ethyl acetate was added slowly. After an additional 30 minutes, the solid was isolated by filtration, washed with 1:1 dichloromethane/ethyl acetate and dried in vacuo to afford 1.98 g of the title compound as a fine, light yellow powder.

(B)

(3S)-3-[[(Phenylmethoxy)carbonyl]amino]-2-azetidinone

A stirred suspension of 1.00 g of (3S)-2-oxo-3-[[(phenylmethoxy)carbonyl]amino]-1-azetidinesulfonic acid, 8-hydroxyquinolinium salt in 75 ml of anhydrous ethanol under nitrogen was placed in a 95° C. oil bath. The mixture was refluxed for 20 minutes, then cooled to 20° C. with an ice water bath. The solvent was removed on the rotary evaporator (bath temperature $\geq$ 30° C.). The residue was taken up in 10 ml of water and 80 ml of ethyl acetate. About 600 mg of $MgSO_4$ was added followed by 570 mg of sodium bicarbonate. The mixture was stirred to effect solution. The organic layer was separated, washed with 5 ml of water, and dried over $MgSO_4$. The solvent was evaporated to afford a white solid, which was tranferred to a 25 ml flask with acetone. The acetone was removed in vacuo and the solid residue was suspended in ca. 5 ml of ethyl acetate. Ether (ca. 6 ml) was added and the mixture was stored for 60 minutes at 0° C. The solid was isolate by filtration, washed with ether, and dried in vacuo to afford 392 mg of the title compound as a white solid.

What is claimed is:

1. A process for preparing a compound having the formula

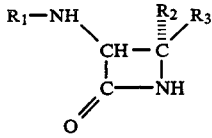

which comprises heating a solution containing an anion having the formula

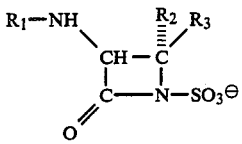

and a cation having the formula

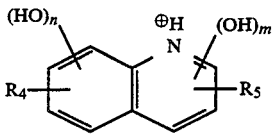

or a cation having the formula

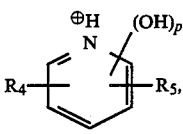

with the proviso that if the cation used does not contain a hydroxy substituent, a nucleophile having the formula

R₆—OH must also be present, wherein

R₁ is an acyl group derived from a carboxylic acid; R₂ and R₃ are the same or different and each is hydrogen, alkyl, alkenyl, alkynyl, cycloalkyl, phenyl, substituted phenyl or a 4, 5, 6 or 7-membered heterocycle, or one of R₂ and R₃ is hydrogen and the other is azido, halomethyl, dihalomethyl, trihalomethyl, alkoxycarbonyl, 2-phenylethenyl, 2-phenylethynyl,

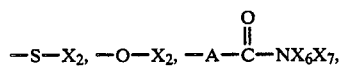

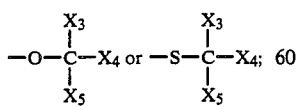

wherein X₁ is azido, amino, hydroxy, alkanoylamino, phenylcarbonylamino, (substituted phenyl)carbonylamino, alkylsulfonyl- oxy, phenylsulfonyloxy, (substituted phenyl)sulfonyloxy, phenyl, substituted phenyl, cyano,

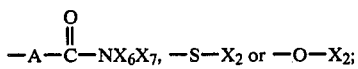

X₂ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl; one of X₃ and X₄ is hydrogen and the other is hydrogen or alkyl, or X₃ and X₄ when taken together with the carbon atom to which they are attached form a cycloalkyl group; X₅ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —(CH₂)ₙ—, —CH₂—O—, —CH₂—NH— or —CH₂—S—CH₂; n is 0, 1 or 2; and X₆ and X₇ are the same or different and each is hydrogen, alkyl, phenyl or substituted phenyl, or X₆ is hydrogen and X₇ is amino, substituted amino, alkanoylamino or alkoxy, or X₆ and X₇ when taken together with the nitrogen atom to which they are attached form a 4, 5, 6 or 7-membered heterocycle;

R₄ and R₅ are the same or different and each is hydrogen, alkyl, substituted alkyl, phenyl, substituted phenyl, halogen, alkoxy, phenyloxy, (phenylcarbonyl)oxy, alkanoyloxy, alkanoylamino or (phenylcarbonyl)amino;

R₆ is hydrogen, alkyl, or phenyl; and n is 0 or 1, m is 0 or 1 and the sum of n+m is 0 or 1; wherein the terms "alkyl" and "alkoxy" refer to groups having 1 to 10 carbon atoms;

the term "cycloalkyl" refers to groups having 3, 4, 5, 6 or 7 carbon atoms;

the term "substituted alkyl" refers to alkyl groups substituted with one or more azido, amino, halogen, hydroxy, carboxyl, cyano, alkoxycarbonyl, aminocarbonyl, alkanyoyloxy, alkoxy, phenyloxy, (substituted phenyl)oxy, mercapto, alkylthio, phenylthio, (substituted phenyl)thio, alkylsulfinyl or alkylsulfonyl groups;

the terms "alkanoyl", "alkenyl" and "alkynyl" refer to groups having 2 to 10 carbon atoms;

the term "substituted phenyl" refers to a phenyl group substituted with 1, 2 or 3 amino halogen, hydroxyl, trifluoromethyl, alkyl of 1 to 4 carbon atoms, alkoxy of 1 to 4 carbon atoms or carboxyl groups;

the term "substituted amino" refers to a group having the formula —NY₁Y₂ wherein Y₁ is hydrogen, alkyl, phenyl, substituted phenyl, phenylalkyl or (substituted phenyl)alkyl and Y₂ is alkyl, phenyl, substituted phenyl, phenylalkyl, (substituted phenyl)alkyl, hydroxy, cyano, alkoxy, phenylalkoxy or amino;

the term "heteroaryl" refers to pyridinyl, furanyl, pyrrolyl, thienyl, 1,2,3,-triazolyl, 1,2,4-triazolyl, imidazolyl, thiazolyl, thiadiazolyl, pyrimidinyl, oxazolyl, triazinyl, or tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl or substituted alkyl, wherein the alkyl group has 1 to 4 carbon atoms, groups; and the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazoyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups.

2. A process in accordance with claim 1 wherein the anion and cation are in the form of a salt having the formula

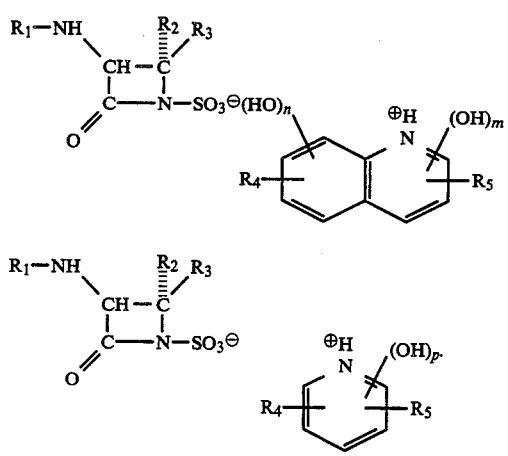

3. A process in accordance with claim 1 wherein the anion and cation are in the form of a salt having the formula

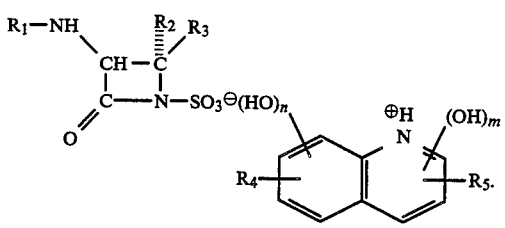

4. A process in accordance with claim 1 wherein the anion and cation are in the form of a salt having the formula

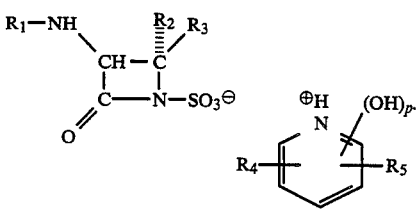

5. A process in accordance with claim 3 wherein the anion and cation are in the form of a salt having the formula

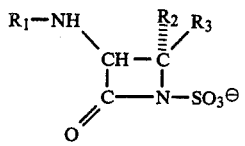 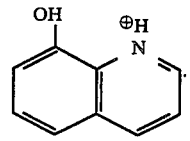

6. A process in accordance with claim 3 wherein the anion and cation are in the form of a salt having the formula

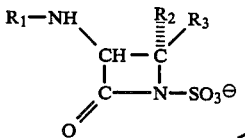 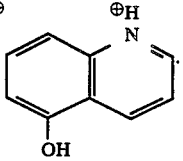

7. A process in accordance with claim 4 wherein the anion and cation are in the form of a salt having the formula

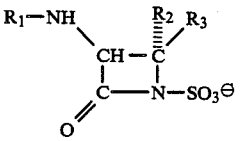 

8. A process in accordance with claim 1 wherein one of $R_2$ and $R_3$ is hydrogen and the other is methyl.

9. A process in accordance with claim 2 wherein one of $R_2$ and $R_3$ is hydrogen and the other is methyl.

10. A process in accordance with claim 1 wherein $R_2$ and $R_3$ are each hydrogen.

11. A process in accordance with claim 2 wherein $R_2$ and $R_3$ are each hydrogen.

12. A process in accordance with claim 1 wherein one of $R_2$ and $R_3$ is hydrogen and the other is

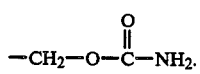

13. A process in accordance with claim 2 wherein one of $R_2$ and $R_3$ is hydrogen and the other is

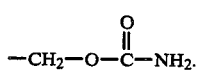

14. A process in accordance with claim 2 wherein $R_1$ is t-butyloxycarbonyl or (phenylmethoxy)carbonyl.

15. A process in accordance with claim 1 wherein the anion is in the form of a basic salt of a compound having the formula

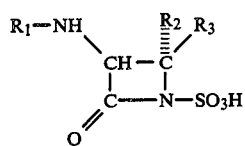

and the cation is in the form of an acid addition salt of a compound having the formula

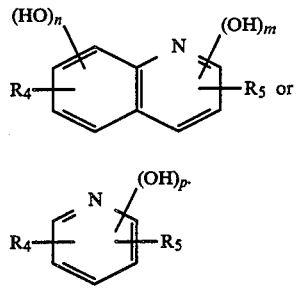

16. A process in accordance with claim 15 wherein the cation is in the form of an acid addition salt of a compound having the formula

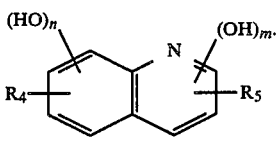

17. A process in accordance with claim 15 wherien the cation is in the form of an acid addition salt of 8-hydroxyquinoline.

18. A process in accordance with claim 15 wherein the cation is in the form of an acid addition salt of a compound having the formula

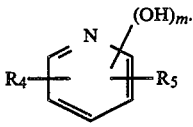

19. A process in accordance with claim 18 wherein the cation is in the form of an acid addition salt of pyridine.

20. A process in accordance with claim 18 wherein the cation is in the form of an acid addition salt of pyridine and the nucleophile used is ethanol.

* * * * *

UNITED STATES PATENT AND TRADEMARK OFFICE
CERTIFICATE OF CORRECTION

PATENT NO. : 4,587,051

DATED : May 6, 1986

INVENTOR(S) : William H. Koster

It is certified that error appears in the above-identified patent and that said Letters Patent is hereby corrected as shown below:

Column 14, line 54, " $\geq$ " should be -- $\leq$ --.

Column 15, line 52, after "2-phenylethynyl", please add -- $CH_2X_1$, carboxyl, --.

Signed and Sealed this

Seventh Day of October, 1986

[SEAL]

*Attest:*

DONALD J. QUIGG

*Attesting Officer*  *Commissioner of Patents and Trademarks*